United States Patent [19]

Lundelius

[11] Patent Number: 4,860,560
[45] Date of Patent: Aug. 29, 1989

[54] RESTRAINING DEVICE

[76] Inventor: William Lundelius, 31277 Meadowbrook Ave., Hayward, Calif. 94544

[21] Appl. No.: 81,977

[22] Filed: Aug. 5, 1987

[51] Int. Cl.$^4$ ............................................. E05B 75/00
[52] U.S. Cl. ........................................ 70/16; 128/846; 128/876
[58] Field of Search .................... 70/15, 16, 14, 17, 18; 128/131 X, 846, 869, 870, 873–876; 119/96, 109

[56] References Cited

U.S. PATENT DOCUMENTS

| | | | |
|---|---|---|---|
| 312,085 | 2/1885 | Claghorn | 119/96 |
| 349,696 | 9/1886 | Davis | 70/16 |
| 380,441 | 4/1888 | Hyatt et al. | 70/16 |
| 583,796 | 6/1897 | Ferrell | 70/16 |
| 787,430 | 4/1905 | Bonnel et al. | 70/16 |
| 1,047,457 | 12/1912 | Steimer | 70/16 |
| 1,082,230 | 12/1913 | Nagle | 70/16 |
| 1,288,170 | 12/1918 | Pick | 119/96 |
| 1,310,958 | 7/1919 | O'Connor | 128/875 X |
| 1,881,948 | 10/1932 | Rayburn | 70/16 |
| 2,006,743 | 7/1935 | Nagle | 70/16 |
| 2,324,183 | 7/1943 | Wilson | 70/16 |
| 3,004,519 | 10/1961 | Weissman | 119/96 |
| 3,046,982 | 7/1962 | Davis | 128/134 |
| 3,536,068 | 10/1970 | Stubbs | 128/134 |
| 4,434,793 | 3/1984 | Willits | 128/134 |
| 4,610,244 | 9/1986 | Hammond | 128/134 X |

FOREIGN PATENT DOCUMENTS 672350  10/1963  Canada ................................ 119/96

*Primary Examiner*—Lloyd A. Gall
*Attorney, Agent, or Firm*—Robert R. Tipton

[57] ABSTRACT

A device for restraining a person utilizes a belt adapted to be attached to the waist of the person being restrained with a pair of right and left arm restraining members attached to the person's wrists. The end of each arm restraining member distal the wrists is slidably connected to the belt and permits the hands to move a predetermined distance longitudinally along the respective right and left sides of the belt. A device is provided for locking the arm restraining members in the forward position. The restraining device permits use of the hands for personal needs while restraining any arm movements that can be violent in nature.

2 Claims, 3 Drawing Sheets

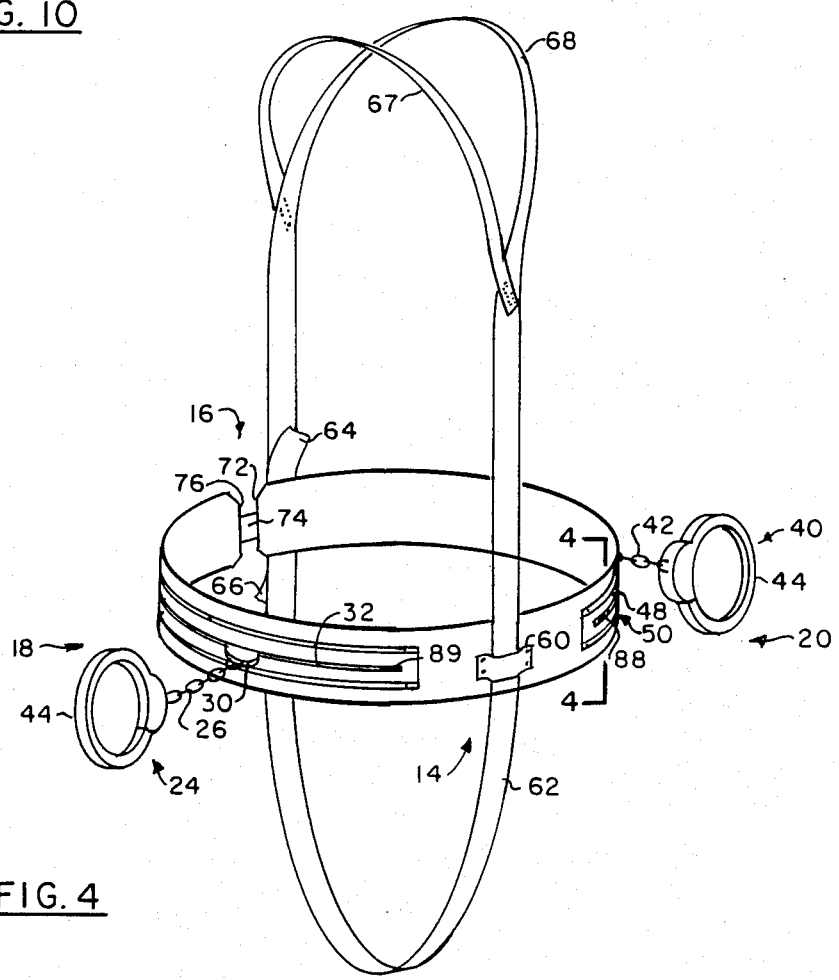
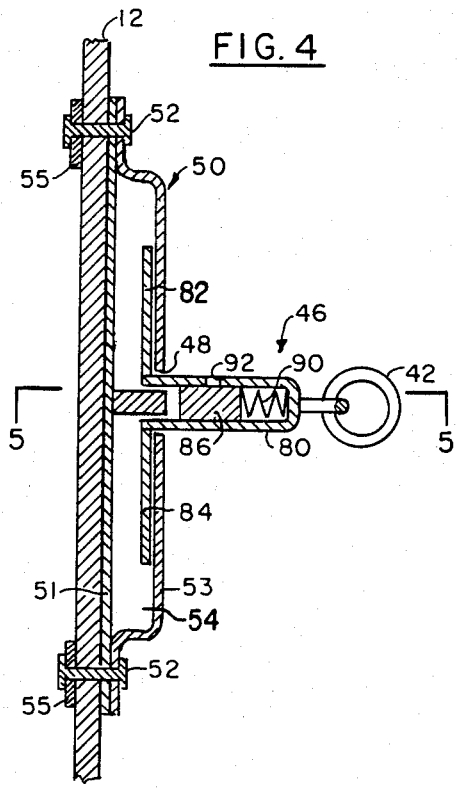
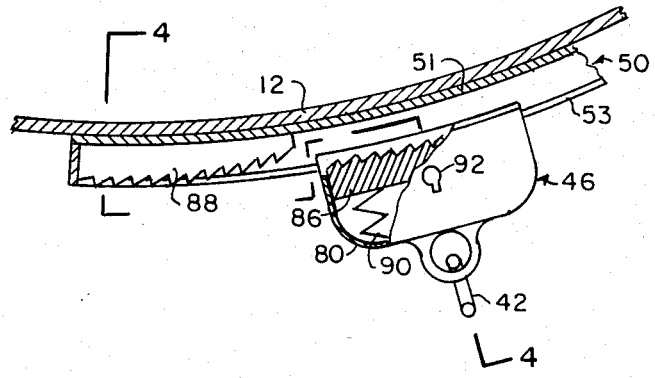

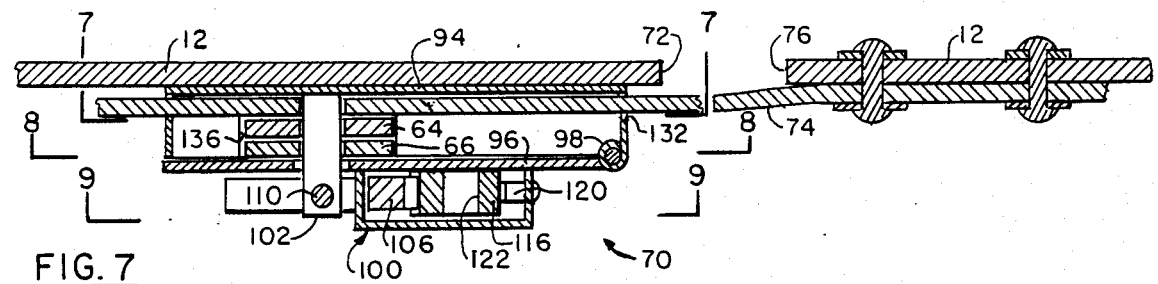
FIG. 6
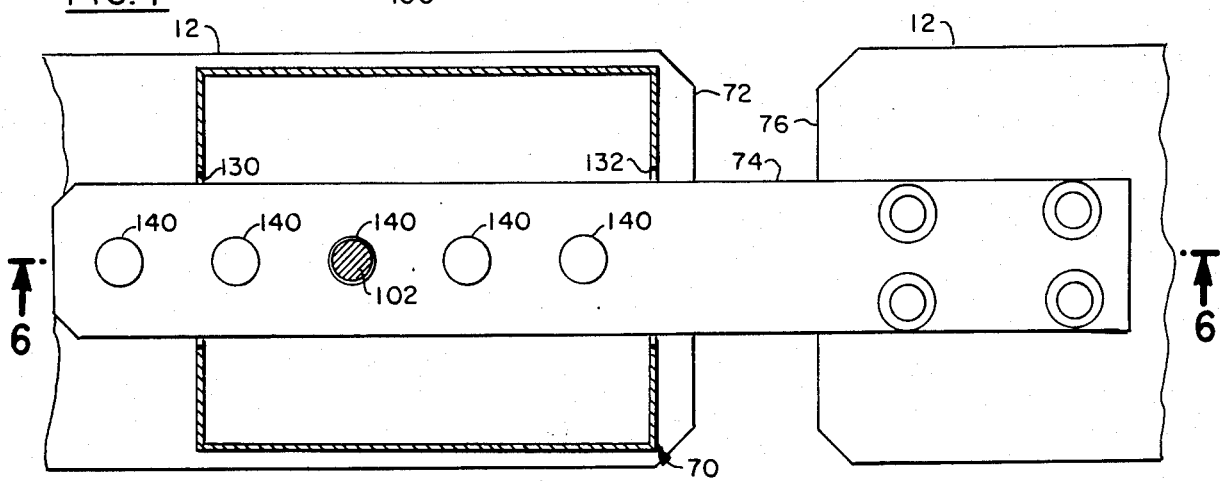
FIG. 7
FIG. 8
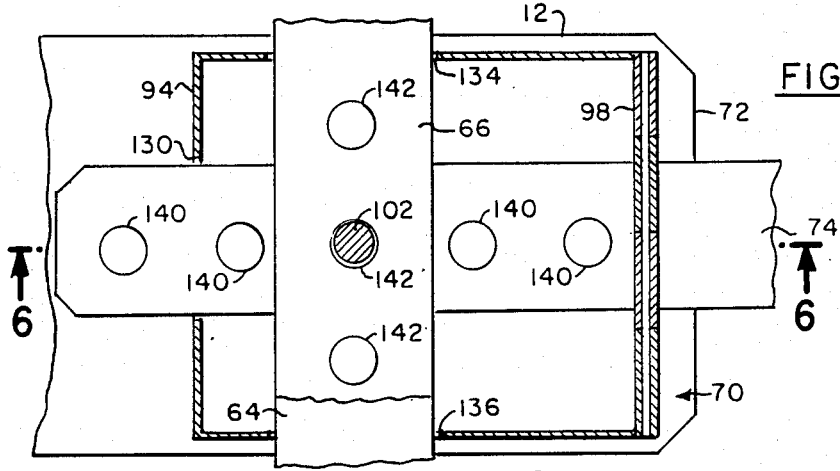
FIG. 9

RESTRAINING DEVICE

BACKGROUND OF THE PRIOR ART

This invention relates generally to restraining devices and in particular to human restraining devices permitting limited arm and hand movement.

When transporting violent prisoners or mental patients, it is necessary to restrain arm movement yet allow a certain amount of hand movement so that the person being restrained can attend to personal needs such as eating and elimination. Furthermore, in the event of an accident, particularly with respect to aircraft, is necessary to provide enough hand movement for the person to remove any objects, such as, seat belts, that might cause him to be trapped in the damaged aircraft.

One prior art device used a belt attached about the waist of the person on which loops were attached. A chain, whose ends were attached to the wrists of the person being restrained, passed through the loops on the belt and around the person's neck. Although the arms were held in a natural position, the hands could not be brought nearer to each other or used for personal needs.

Other restraining devices used a belt and handcuffs that were attached at a fixed point along the belt. Hand and arm movement was determined solely according to the length of the chain or straps connecting the handcuffs to the belt.

None of the prior art devices permitted limited arm movement to restrain violent moves while allowing extended movement of the hands for taking care of personal needs.

SUMMARY OF THE INVENTIONS

The device of the present invention comprises, basically, a belt adapted to be placed and fastened about the waist of the person being restrained and a pair of right and left arm restraining members having one end attached, respectively, to the wrists of the person and with the other end connected, respectively, to the right and left sides of the belt and allowed to move a predetermined distance back and forth longitudinally along the sides of the belt. A latching means is provided for locking the arm restraining member in the forward position. The restraining device limits the distance the arms of the person can be raised and lowered while permitting front and rear movement of the hands sufficient to take care of personal needs or when transferring a person from ordinary handcuffs to the restraining device of the present invention.

It is, therefore, an object of the present invention to provide a device for restraining a person that permits restraint of violent are movement while allowing sufficient movement of the hands for personal needs.

It is a further object of the present invention to provide a device for restraining a person in which vertical arm movement is restrained while permitting horizontal movement of the hands.

It is yet another object of the present invention to provide a device for restraining a person in which the arm restraining members are slidably connected to the belt encircling the person.

It is still another object of the present invention to provide a device for restraining a person in which the arm restraining members are slidably connected to the belt encircling the person and automatically latchable in the forward position.

It is a further object of the present invention to provide a device for restraining a person in which the hands are allowed to move a predetermined distance back and forth along each side of the person.

These and other objects of the present invention will become manifest upon study of the following detailed description when taken together with the drawings.

BRIEF DESCRIPTION OF THE DRAWINGS

FIG. 4 is an elevational cross-section of the restraining device of the present invention taken at line 4—4 of FIG. 10 showing how the belt connector member is connected to the side connector plate and latched in the forward position.

FIG. 5 is, a cross-sectional, plan view of the front latching members taken at line 5—5 of FIG. 4.

FIG. 6 is a cross-sectional, plan view of the belt closure fastening member of the present invention taken at line 6—6 of FIGS. 7, 8 and 9.

FIG. 7 is a cross-sectional, elevational view of the belt closure fastening member of the present invention taken at line 7—7 of FIG. 8 is a cross-sectional, elevational view of the belt closure fastening member of the present invention taken at line 8—8 of FIG. 6.

FIG. 9 is a cross-sectional, elevational view of the belt closure fastening member of the present invention taken at line 9—9 of FIG. 6.

FIG. 10 is an isometric view of the assembled restraining device of the present invention as would be worn by the person being restrained.

DESCRIPTION OF THE PREFERRED EMBODIMENT

Figure 1:
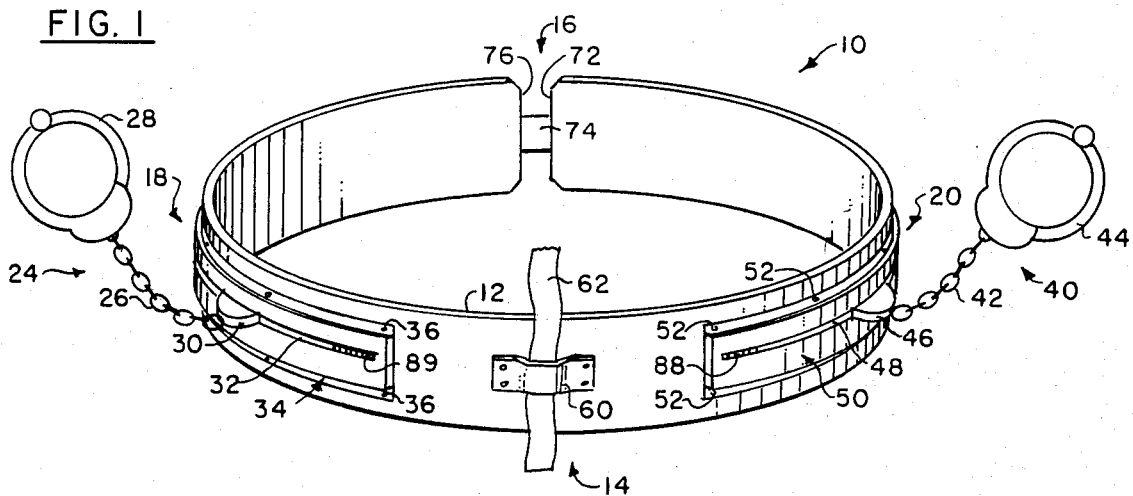
FIG. 1 is an isometric view of the front of the restraining device of the present invention.
Figure 2:
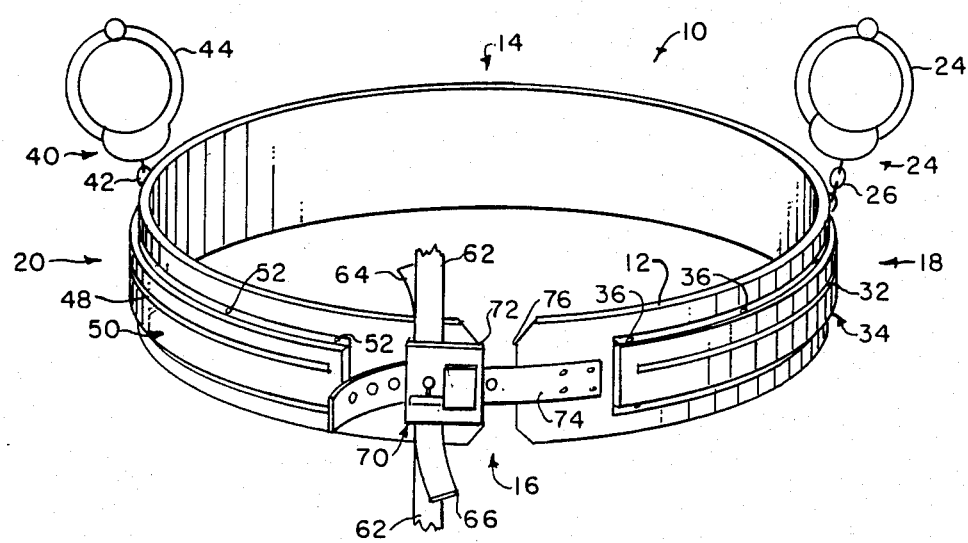
FIG. 2 is an isometric view of the back of the restraining device of the present invention.
Figure 3:
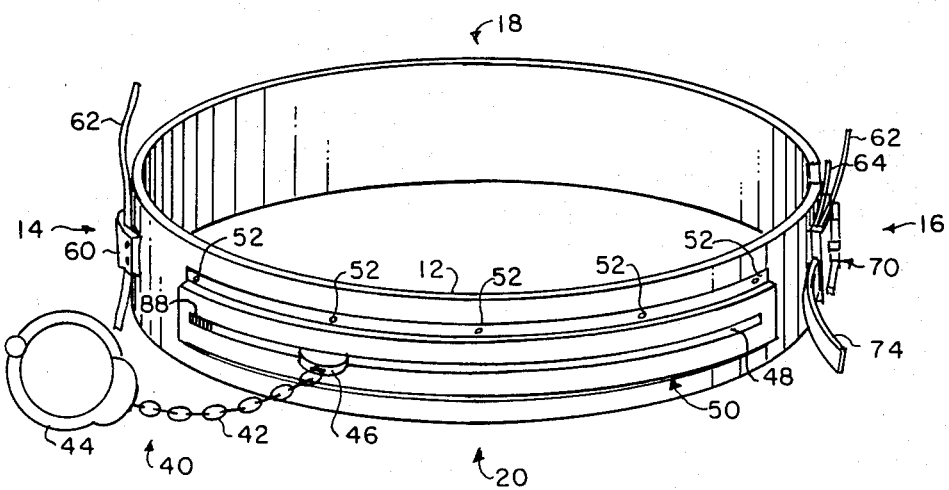
FIG. 3 is an isometric view of the left side of the restraining device of the present invention.

With reference to FIGS. 1, 2 and 3 there are illustrated isometric views of the front, back and left side, respectively, of the restraining device 10 of the present invention.

Restraining device 10 comprises, basically, generally flexible belt 12 having a front side 14, a back or rear side 16, a right side 18 and a left side 20.

Belt 12 can be fabricated from a suitably flexible, yet strong material such as leather, woven web material or the like.

Restraining device 10 further comprises a right arm restraining member 24, including a chain 26 having a right handcuff 28 attached to one end and a right belt connector member 30 connected to the other end. Right belt connector member 30 is adapted to slidably engage right slot 32 in right side connector plate 34 attached as by rivets 36, or the like, to the right side of belt 12.

In a similar manner restraining device 10 further comprises a left arm restraining member 40 including a chain 42 having a left handcuff 44 attached to one end and a left belt connector member 46 connected to the other end. Left belt connector member 46 is adapted to slidably engage left slot 48 in left side connector plate 50 attached as by rivets 52, or the like, to the left side of belt 12.

With reference to FIG. 4 and 5, there is illustrated a cross-sectional, elevational view of side connector plate 50 taken at line 4—4 of FIG. 10 FIG. 5 illustrates a cross-sectional, plan view of side connector plate 50 taken at line 5—5 of FIG. 4.

It should be noted that FIGS. 4 and 5 illustrate the method of connecting left arm restraining member 40 to left side connector plate 50 and how it is latched in the forward position. The method of connecting right arm restraining member 24 to right side connector plate 34 will be identical and the mirror image of that shown in FIGS. 4 and 5.

Side connector plate 50 comprises, basically, a base connector plate 51 placed in contact with flexible belt 12 and channel connector plate 53 in which the top and bottom edges have been bent to define a channel 54 running the length of side connector plate 50. The top and bottom edges of channel connector plate 53 are attached to the top and bottom edges of base connector plate 51 as by welding or the like.

Side connector plate 50 is attached to belt 12 as by rivets 52 or the like.

A slot 48 is provided in channel connector plate 53 to permit belt connector member 46 to be received in and be slidably engaged thereby and, as can be seen from FIG. 3, to limit or restrict the movement of connector member 46 to the length of slot 48.

Side connector plates 34 and 50 can be fabricated from a rigid metal such as steel or the like. It should be of sufficient thickness and strength to resist bending due to lateral arm forces of the person being restrained. A metal reinforcing washer 55 (FIG. 4) along the inside of belt 12 can be used to prevent lateral forces from pulling rivets 52 out of flexible belt 12.

With reference to FIG. 4, belt connector member 46 comprises, basically, connector housing 80 adapted to slidably engage slot 48 with top and bottom connector guide members 82 and 84, respectively, attached to the top and bottom edges of connector housing 80 inside channel 54. Top and bottom guide members 82 and 84 assist in guiding belt connector member 46 along slot 48 and well as providing a bearing surface along the inside of channel connector member 53 to resist any lateral forces tending to pull connector member 46 out of slot 48.

A connector latching member 86 is provided within housing 80 adapted to engage left fixed end latching member 88 attached to base connector plate 51. (A corresponding right fixed end latching member 89 (FIG. 10) is shown for right side connector plate 34).

A spring 90 is provided to bias connector latching member 86 against fixed end latching member 88.

A keyhole 92 and means common in the art (not shown) are used to move connector latch member 86 away from fixed latch member 88 in order to release connector latch member 86, of left belt connector 46, from fixed latch member 88.

With particular reference to FIG. 1, a front strap guide 60 is provided to engage neck/crotch strap 62, seen in full view in FIG. 10.

With particular reference to FIG. 2, a belt closure fastening member 70 is attached to the back of belt 12 proximate end 72, and is adapted to engage belt strap 74 attached to the other end 76 of belt 12.

Belt closure fastening member 70 is also adapted to engage ends 64 and 66 of neck/crotch strap 62 which pass vertically through belt closure fastening member 70 at a right angle to belt strap 74.

With reference to FIG. 6 belt closure fastening member 70 comprises, basically, a belt lock support housing 94 having closure door 96 connected thereto by hinge 98. A door latching device 100 is attached to closure door 96.

Strap connector pin 102 is attached, as by welding or the like, to belt lock support housing 94. A hole 103 is provided in door 96 of sufficient diameter to clear strap connector pin 102 when door 96 is closed.

With reference to FIGS. 6 and 9, door latching device 100 comprises, basically, a latch housing 104 containing first latch member 106 adapted to move vertically and having a pin 108 adapted to engage hole 110 (FIG. 6) in strap connector pin 102.

First latch member 106 further comprises a set of ratchet teeth 112 adapted to engage like ratchet teeth 114 in second latch member 116.

Second latch member 116 is pivotally connected to closure door 96 by pivot pin 118. It is biased against ratchet teeth 112 of first latch member 106 by string 120.

A key slot 122 is provided in second latch member 116 to allow key 124 to rotate second latch member 116 away from ratchet teeth 112 of first latch member 106 thus releasing first latch member 106 and allow it to fall and release pin 108 from hole 110 in strap connector pin 102. In so doing, closure door 96 can be opened for access to strap connector pin 102.

With reference to FIG. 7, belt lock support housing 94 further comprises first and second slots 130 and 132 in the vertical sides of belt lock support housing 94 adapted to receive belt strap 74.

With reference to FIGS. 7 and 8, belt lock support housing 94 further comprises third and fourth slots 134 and 136 in top and bottom sides of belt lock support housing 94 adapted to receive ends 64 and 66 of neck/crotch strap 62.

OPERATION:

To install restraining device 10 on a person to be restrained, reference is made to FIG. 10. FIG. 10 is an isometric view of the assembled restraining device 10 of the present invention.

In many cases, the person being restrained will already be handcuffed with his hands either in back or in front of his body. In describing how the restraining device of the present invention is used, it will be assumed that the person being restrained will be handcuffed with his hands behind his back.

First, restraining device 10 of the present invention is placed with belt 12 around the waist of the person being restrained with belt closure fastening member 70 proximate the back of the person being restrained.

When opening belt 12, since it is fabricated from a flexible material, front side 14 will flex to act as a hinge for rigid sides 18 and 20.

Belt strap 74 is passed horizontally through slots 130 and 132 of belt closure fastening member 70 with a selected hole 140 in strap 74 placed to engage strap connector pin 102.

Where a crotch/neck strap s required, end 64 of neck/crotch strap 62 is passed through front strap guide 60 proximate the front side 14 of belt 12 to be held in the front position and guided thereby. End 64 is then passed through the crotch of the person being restrained and connected to strap connector pin 102 of belt closure fastening member 70.

The other end 66 of neck/crotch strap 62 is passed over the head of the person being restrained with bifurcated or separate strap portions 67 and 68 of neck/crotch strap 62 passing around the neck of the person being restrained. End 66 of neck/crotch strap 62 is then connected to strap connector pin 102 of belt closure fastening member 70.

With both ends 64 and 66 of neck/crotch strap 62 and belt strap 74 placed over each other, using a selected hole 142, on strap connector pin 102, belt latch door 96 is then closed thus locking straps 74 and 62 in place.

First latch member 106 is pushed upward to cause ratchet teeth 112 and 114 to engage and hold pin 108 in engagement with hole 110 in strap connector pin 102 thus locking closure door 96

The wrists of the person being restrained are then placed in handcuffs 28 and 44 and the previously applied handcuffs (not shown) are removed.

The person being restrained is then allowed to move his hands back and forth about his sides but is restrained by device 10 of the present invention from moving is hands and arms up or down as would be the normal motion of he were to make any violent moves.

As soon as the person being restrained moves his hands to the forward position, pulling arm restraining members 24 and 40 with them, latching members in left and right belt connector members 46 and 30, respectively, with engage their respective fixed latch members 88 and 89 thus locking arm restraint members 40 and 24 in the forward position.

In this position the person being restrained can take care of most of his personal needs.

In certain instances where the person being restrained must have his arms at his side or in back, such as, when he must be examined by a doctor, make an appearance in court, or the like, left and right side belt connector members 46 and 24 may be unlocked from connector member 88 and 89 to allow the person being restrained to move his arms to the side.

It should be noted that, under certain circumstances, it may not be necessary to use neck/crotch strap 62. For a person of normal girth, belt 12 can be tightened, without discomfort to the person being restrained, so this vertical movement along the body of the person being restrained will be limited.

The use of neck/crotch strap 62 would be appropriate in certain cases, for example, if upward movement of the belt were too great and the person being restrained could use his arms and elbows as weapons.

It would also be appropriate if the girth of the person being restrained were too great and it were possible to slide belt 10 over the hips and allow the person being restrained to remove the belt from his body.

Although the restraining device of the present invention has been described in detail, this description is not intended to limit the scope of this invention except as defined by the claims.

I claim:

1. A device for restraining a person comprising
 a belt adapted to be fastened around the waist of said person being restrained, said belt having front, back, right and left sides,
 an arm restraining member comprising
 means for attaching said arm restraining member proximate the wrist of said person being restrained,
 means for restricting said arm restraining member to move a predetermined distance back and forth along the side of said belt, said means for restricting comprising
 a belt connector member slidably connected to said belt and restricted to move a predetermined distance along the side thereof,
 said predetermined distance being sufficient to permit the attachment of other arm restraining devices to said person being restrained when said arm restraining member is positioned proximate the back of said belt, and
 means for connecting said belt connector member to said arm restraining member,
 means for locking said arm restraining member proximate a predetermined position along the length of said means for restricting said arm restraining member to move a predetermined distance back and forth along a side of said belt.

2. A device for restraining a person comprising
 a belt adapted to be fastened around the waist of a person being restrained, said belt having front, back, right and left sides,
 a right arm restraining member comprising
 means for attaching one end of said right arm restraining member proximate the right wrist of said person being restrained,
 means for connecting the other end of said right arm restraining member to the right side of said belt, and
 means for allowing said means for connecting the other end of said right arm restraining member to the right side of said belt to move a predetermined distance back and forth along the right side of said belt,
 a left arm restraining member comprising
 means for attaching one end of said left arm restraining member proximately the left wrist of said person being restrained,
 means for connecting the other end of said left arm restraining member to the left side of said belt, and
 means for allowing said means for connecting the other end of said left arm restraining member to the left side of said belt to move a predetermined distance back and forth along the left side of said belt,
 means for preventing said belt from being removed from the waist of said person being restrained comprising
 a strap comprising
 a first end,
 a second end, and
 a bifurcated portion adapted to pass over the head and around the neck of the person being restrained,
 means for connecting said strap proximate the front portion of said belt,
 means for connecting said first end proximate the back portion of said belt, and
 means for connecting said second end proximate the back portion of said belt. portion of said belt, and
 means for connecting said second end proximate the back portion of said belt.

* * * * *